(12) United States Patent
James

(10) Patent No.: US 11,519,915 B1
(45) Date of Patent: *Dec. 6, 2022

(54) METHOD FOR TRAINING AND TESTING SHORTCUT DEEP LEARNING MODEL CAPABLE OF DIAGNOSING MULTI-CANCER USING BIOMARKER GROUP-RELATED VALUE INFORMATION AND LEARNING DEVICE AND TESTING DEVICE USING THE SAME

(71) Applicant: KKL CONSORTIUM LIMITED, Tortola (VG)

(72) Inventor: Lancelot Fitzgerald James, Hong Kong (HK)

(73) Assignee: KKL Consortium Limited, Tortola (VG)

(*) Notice: Subject to any disclaimer, the term of this patent is extended or adjusted under 35 U.S.C. 154(b) by 0 days.

This patent is subject to a terminal disclaimer.

(21) Appl. No.: 17/511,750

(22) Filed: Oct. 27, 2021

(51) Int. Cl.
*G01N 31/00* (2006.01)
*G01N 33/53* (2006.01)
*G01N 33/574* (2006.01)
*G16H 50/20* (2018.01)

(52) U.S. Cl.
CPC ....... *G01N 33/57407* (2013.01); *G16H 50/20* (2018.01)

(58) Field of Classification Search
None
See application file for complete search history.

(56) References Cited

U.S. PATENT DOCUMENTS

2021/0142904 A1* 5/2021 Michuda ................ G16H 50/20
2021/0233611 A1* 7/2021 Brewer ................. G16B 25/10

* cited by examiner

*Primary Examiner* — Lisa V Cook
(74) *Attorney, Agent, or Firm* — Taft Stettinius & Hollister LLP

(57) ABSTRACT

A deep learning based diagnostic model capable of diagnosing multi-cancer using biomarker group-related value information is trained by using a method including steps of: in response to acquiring training data including the biomarker group-related value information and GT (Ground Truth) cancer information for each of patients, inputting the training data into the diagnostic model and then instructing the diagnostic model to (i) allow each hidden layer, among a first hidden layer to a K-th hidden layer, to perform a fully connected operation on its previous sub input values for training obtained from its previous hidden layer, wherein K is an integer greater than or equal to 1, and then (ii) allow an output layer to perform a fully connected operation on K-th sub input values for training obtained from the K-th hidden layer, to thereby output multi-cancer diagnosis information for training as a result of predicting multi-cancer.

10 Claims, 4 Drawing Sheets

METHOD FOR TRAINING AND TESTING SHORTCUT DEEP LEARNING MODEL CAPABLE OF DIAGNOSING MULTI-CANCER USING BIOMARKER GROUP-RELATED VALUE INFORMATION AND LEARNING DEVICE AND TESTING DEVICE USING THE SAME

FIELD OF THE DISCLOSURE

The present disclosure relates to a method for training and testing a shortcut deep learning model capable of diagnosing multi-cancer using biomarker group-related value information, and a learning device and a testing device using the same; and more particularly, to the method for training a deep learning based diagnostic model capable of diagnosing multi-cancer such that some data related to easily classifiable cancers among the multi-cancer are simply calculated through a shortcut layer and other some data related to difficultly classifiable cancers among the multi-cancer are calculated through hidden layers by using the biomarker group-related value information.

BACKGROUND OF THE DISCLOSURE

Tumor metastasis represents that some portion of a tumor is detached from a part of the body of patient and moves to other parts of the body via blood, which is an important cause of cancer-related death. A general way of diagnosing a tumor status is a biopsy which detaches and examines a part of tissue in an early stage of metastasis. It is, however, not easy to determine an exact part of the body from which the tissue is removed. As an alternative way, a liquid biopsy attracting attention in recent years can detect tumor cells in a biological sample such as blood, urine, etc. derived from a patient's body. According to the liquid biopsy, a cancer in the early stage can be detected and diagnosed and additionally a progression of cancer and its corresponding cure can be monitored.

A biomarker is a measurable indicator of some biological state or condition. Biomarkers are often measured and evaluated using blood, urine, or soft tissues to examine normal biological processes, pathogenic processes, or pharmacologic responses to a therapeutic intervention. The biomarkers can detect changes in the body by using proteins, nucleic acids, and metabolites contained in biological samples.

However, since there is a limit in diagnosing cancer with a biomarker, a cancer diagnosing method using a complex biomarkers with an improvement in diagnostic sensitivity and specificity is currently used in this field.

However, in case of predicting a certain cancer by using such complex biomarkers, a specific biomarker included in the complex biomarkers may not only represent an indicator for the certain cancer but also represent another indicator for another cancer. Thus, the certain cancer may be wrongly predicted by using the complex biomarkers.

As an example, it may indicate the adenocarcinoma as a result of prediction by using biomarker group-related value information derived from the complex biomarkers, although a patient's cancer is actually squamous cell carcinoma.

Also, in predicting a cancer by using the biomarker group-related value information of the complex biomarkers, there is a possibility of acquiring a different result according to a doctor in charge.

In order to solve the aforementioned issues, various studies on deep learning based diagnostic models for classifying cancers using biomarker group-related value information of complex biomarkers are being conducted.

Such a deep learning based diagnostic model has a complex structure with multiple hidden layers because it is necessary to accurately classify the multi-cancer even when it is difficult to distinguish one or more cancers among the multi-cancer by using the biomarker group-related value information.

However, among cancers to be classified using the biomarker group-related value information, there are some cancers that are relatively easy to classify.

Additionally, among the biomarker group-related value information, there are some specific data that may reliably diagnose cancers.

Therefore, it is inefficient to classify some data related to easily classifiable cancers by using a deep-learning based diagnostic model of the complex structure with multiple hidden layers.

Accordingly, the applicant of the present disclosure proposes to provide a deep learning based diagnostic model that can easily classify some data related to easily classifiable cancers through a simpler structure, and classify other some data related to difficultly classifiable cancers through a complex structure.

SUMMARY OF THE DISCLOSURE

It is an object of the present disclosure to solve all the aforementioned problems.

It is another object of the present disclosure to provide a deep learning based diagnostic model that can classify data related to easily classifiable cancers through a simpler structure, and classify other data related to difficultly classifiable cancers through a complex structure.

It is still another object of the present disclosure to accurately identify various types of cancers by using biomarker group-related value information for diagnosing multi-cancer.

It is still yet another object of the present disclosure to accurately identify the various types of cancers by implementing a statistical discrimination method using the biomarker group-related value information.

It is still yet another object of the present disclosure to improve a reliability in classifying the various types of cancers by implementing the statistical discrimination method using the biomarker group-related value information.

In order to accomplish objects above and characteristic effects to be described later of the present disclosure, distinctive structures of the present disclosure are described as follows.

In accordance with one aspect of the present disclosure, there is provided a method for training a deep learning based diagnostic model capable of diagnosing multi-cancer using biomarker group-related value information, including steps of: (a) a learning device, in response to acquiring training data including the biomarker group-related value information and GT (Ground Truth) cancer information for each of patients, inputting the training data into the diagnostic model and then instructing the diagnostic model to (i) allow each hidden layer, among a first hidden layer to a K-th hidden layer, to perform a fully connected operation on its previous sub input values for training obtained from its previous hidden layer, wherein K is an integer greater than or equal to 1, and then (ii) allow an output layer to perform a fully connected operation on K-th sub input values for training obtained from the K-th hidden layer, to thereby output multi-cancer diagnosis information for training as a result of predicting multi-cancer, wherein the learning device instructs the diagnostic model, while changing a value of k from 1 to K−1, (i) to input k-th sub output values for training outputted from a k-th hidden layer into a k-th probability layer and then to allow the k-th probability layer to output each of k-th probability values for training corresponding to each of L number of multi-cancers, (ii) (ii-1) to input the k-th sub output values for training into a k-th shortcut layer and then to allow the k-th shortcut layer to perform a fully connected operation on the k-th sub output values for training and then apply the k-th probability values for training as weights to a result of performing the fully connected operation on k-th sub output values for training, to thereby output k-th shortcut sub output values for training, and (ii-2) to input the k-th sub output values for training into a (k+1)-th hidden layer and then to allow the (k+1)-th hidden layer to perform a fully connected operation on the k-th sub output values for training and then apply "1−the k-th probability values for training" as weights to a result of performing the fully connected operation on the k-th sub output values for training, to thereby output a (k+1)-th sub output values for training, and (iii) to allow the output layer to perform the fully connected operation on (iii-1) the K-th sub output values for training outputted from the K-th hidden layer and (iii-2) a first shortcut sub output values for training outputted from a first shortcut layer to a (K−1)-th shortcut sub output values for training outputted from a (K−1)-th shortcut layer, to thereby output the multi-cancer diagnosis information for training; and (b) the learning device generating losses by referring to the multi-cancer diagnosis information for training outputted from the output layer and the GT cancer information, and backpropagating the losses to update parameters of at least one of the output layer, the K-th hidden layer to the first hidden layer, a (K−1)-th shortcut layer to a first shortcut layer, and a (K−1)-th probability layer to a first probability layer.

As one example, at the step of (a), the learning device instructs the diagnostic model to input the k-th sub output values for training into the k-th probability layer and then to allow each of a (k_1)-th probability node of the k-th probability layer to a (k_L)-th probability node of the k-th probability layer, respectively corresponding to each of a first output node of the output layer related to a first cancer to an L-th output node of the output layer related to an L-th cancer, to perform a fully connected operation on the k-th sub output values for training, to thereby output a (k_1)-st probability value for training corresponding to the first cancer to a (k_L)-th probability value for training corresponding to the L-th cancer, as a result of predicting possibilities of progressing from the k-th hidden layer to the k-th shortcut layer without progressing from the k-th hidden layer to the (k+1)-th hidden layer.

As one example, at the step of (a), the learning device instructs the diagnostic model to input the k-th sub output values for training into the k-th shortcut layer, which includes each of a (k_1)-st shortcut node to a (k_L)-th shortcut node corresponding to each of the first output node to the L-th output node, and then allow a (k_i)-th shortcut node corresponding to an i-th cancer among the (k_1)-st shortcut node to the (k_L)-th shortcut node to perform a fully connected operation on the k-th sub output values for training and then apply a (k_i)-th probability value for training as a weight to a result of performing the fully connected operation on the k-th sub output values for training, to thereby output a (k_i)-th shortcut sub output values for training.

As one example, at the step of (a), the learning device instructs the diagnostic model to allow an i-th output node of the output layer corresponding to the i-th cancer to perform a fully connected operation on (i) the K-th sub output values for training of the K-th hidden layer, and (ii) a (1_i)-th shortcut sub output value for training outputted from a (1_i)-th shortcut node of the first shortcut layer to a ((K−1)_i)-th shortcut sub output value for training outputted from a ((K−1)_i)-th shortcut node of the (K−1)-th shortcut layer, to thereby output i-th cancer diagnosis information for training as a result of predicting the i-th cancer.

As one example, at the step of (a), the learning device instructs the diagnostic model to input the k-th sub output values for training to the (k+1)-th hidden layer, and then to allow each of (k+1)-th hidden nodes of the (k+1)-th hidden layer to perform a fully connected operation on the k-th sub output values for training, and thus to sum each of (i) (k+1)_1-st intermediate sub output values for training, which are acquired by applying "1−the (k_1)-th probability value for training" as a weight to the results of performing the fully connected operation on the k-th sub output values for training, to (ii) (k+1)_L-th intermediate sub output values for training, which are acquired by applying "1−the (k_L)-th probability value for training" as a weight to the results of performing the fully connected operation on the k-th sub output values for training, to thereby output (k+1)-th sub output values for training.

In accordance with another aspect of the present disclosure, there is provided a method for testing a deep learning based diagnostic model capable of diagnosing multi-cancer using biomarker group-related value information, including steps of: (a) a testing device acquiring test data including specific biomarker group-related value information for a specific patient, on condition that the diagnostic model has been trained by a learning device through performing processes of (I) in response to acquiring training data including biomarker group-related value information for training and GT (Ground Truth) cancer information for each of patients for training, inputting the training data into the diagnostic model and then instructing the diagnostic model to (i) allow each hidden layer, among a first hidden layer to a K-th hidden layer, to perform a fully connected operation on its previous sub input values for training obtained from its previous hidden layer, wherein K is an integer greater than or equal to 1, and then (ii) allow an output layer to perform a fully connected operation on K-th sub input values for training obtained from the K-th hidden layer, to thereby output multi-cancer diagnosis information for training as a result of predicting multi-cancer, wherein the learning device instructs the diagnostic model, while changing a value of k from 1 to K−1, (i) to input k-th sub output values for training outputted from a k-th hidden layer into a k-th probability layer and then to allow the k-th probability layer to output each of k-th probability values for training corresponding to each of L number of multi-cancers, (ii) (ii-1) to input the k-th sub output values for training into a k-th shortcut layer and then to allow the k-th shortcut layer to perform a fully connected operation on the k-th sub output values for training and then apply the k-th probability values for training as weights to a result of performing the fully connected operation on k-th sub output values for training, to thereby output k-th shortcut sub output values for training, and (ii-2) to input the k-th sub output values for training into a (k+1)-th hidden layer and then to allow the (k+1)-th hidden layer to perform a fully connected operation on the k-th sub output values for training and then apply "1−the k-th probability values for training" as weights to a result of performing the fully connected operation on the k-th sub output values for training, to thereby output a (k+1)-th sub output values for training, and (iii) to allow the output layer to perform the fully connected operation on (iii-1) the K-th sub output values for training outputted from the K-th hidden layer and (iii-2) a first shortcut sub output values for training outputted from a first shortcut layer to a (K−1)-th shortcut sub output values for training outputted from a (K−1)-th shortcut layer, to thereby output the multi-cancer diagnosis information for training; and (II) generating losses by referring to the multi-cancer diagnosis information for training outputted from the output layer and the GT cancer information, and backpropagating the losses to update parameters of at least one of the output layer, the K-th hidden layer to the first hidden layer, a (K−1)-th shortcut layer to a first shortcut layer, and a (K−1)-th probability layer to a first probability layer; and (b) the testing device inputting the test data into the diagnostic model and then instructing the diagnostic model to (i) allow each hidden layer, among the first hidden layer to the K-th hidden layer, to perform a fully connected operation on its previous sub input values for testing obtained from its previous hidden layer, wherein K is an integer greater than or equal to 1, and then (ii) allow the output layer to perform a fully connected operation on K-th sub input values for testing obtained from the K-th hidden layer, to thereby output multi-cancer diagnosis information for testing as a result of predicting multi-cancer, wherein the testing device instructs the diagnostic model, while changing a value of k from 1 to K−1, (i) to input k-th sub output values for testing outputted from the k-th hidden layer into the k-th probability layer and then to allow the k-th probability layer to output each of k-th probability values for testing corresponding to each of L number of multi-cancers, (ii) (ii-1) to input the k-th sub output values for testing into the k-th shortcut layer and then to allow the k-th shortcut layer to perform a fully connected operation on the k-th sub output values for testing and then apply the k-th probability values for testing as weights to a result of performing the fully connected operation on k-th sub output values for testing, to thereby output k-th shortcut sub output values for testing, and (ii-2) to input the k-th sub output values for testing into the (k+1)-th hidden layer and then to allow the (k+1)-th hidden layer to perform a fully connected operation on the k-th sub output values for testing and then apply "1−the k-th probability values for testing" as weights to a result of performing the fully connected operation on the k-th sub output values for testing, to thereby output a (k+1)-th sub output values for testing, and (iii) to allow the output layer to perform the fully connected operation on (iii-1) the K-th sub output values for testing outputted from the K-th hidden layer and (iii-2) a first shortcut sub output values for testing outputted from the first shortcut layer to a (K−1)-th shortcut sub output values for testing outputted from the (K−1)-th shortcut layer, to thereby output the multi-cancer diagnosis information for testing.

As one example, at the step of (b), the testing device instructs the diagnostic model to input the k-th sub output values for testing into the k-th probability layer and then to allow each of a (k_1)-th probability node of the k-th probability layer to a (k_L)-th probability node of the k-th probability layer to perform a fully connected operation on the k-th sub output values for testing, to thereby output a (k_1)-st probability value for testing corresponding to the first cancer to a (k_L)-th probability value for testing corresponding to the L-th cancer, as a result of predicting possibilities of progressing from the k-th hidden layer to the k-th shortcut layer without progressing from the k-th hidden layer to the (k+1)-th hidden layer.

As one example, at the step of (b), the testing device instructs the diagnostic model to input the k-th sub output values for testing into the k-th shortcut layer, and then allow a (k_i)-th shortcut node corresponding to an i-th cancer among the (k_1)-st shortcut node to the (k_L)-th shortcut node to perform a fully connected operation on the k-th sub output values for testing and then apply a (k_i)-th probability value for testing as a weight to a result of performing the fully connected operation on the k-th sub output values for testing, to thereby output a (k_i)-th shortcut sub output values for testing.

As one example, at the step of (b), the testing device instructs the diagnostic model to allow an i-th output node of the output layer corresponding to the i-th cancer to perform a fully connected operation on (i) the K-th sub output values for testing of the K-th hidden layer, and (ii) a (1_i)-th shortcut sub output value for testing outputted from a (1_i)-th shortcut node of the first shortcut layer to a ((K−1)_i)-th shortcut sub output value for testing outputted from a ((K−1)_i)-th shortcut node of the (K−1)-th shortcut layer, to thereby output i-th cancer diagnosis information for testing as a result of predicting the i-th cancer.

As one example, at the step of (b), the testing device instructs the diagnostic model to input the k-th sub output values for testing to the (k+1)-th hidden layer, and then to allow each of (k+1)-th hidden nodes of the (k+1)-th hidden layer to perform a fully connected operation on the k-th sub output values for testing, and thus to sum each of (i) (k+1)_1-st intermediate sub output values for testing, which are acquired by applying "1−the (k_1)-th probability value for testing" as a weight to the results of performing the fully connected operation on the k-th sub output values for testing, to (ii) (k+1)_L-th intermediate sub output values for testing, which are acquired by applying "1−the (k_L)-th probability value for testing" as a weight to the results of performing the fully connected operation on the k-th sub output values for testing, to thereby output (k+1)-th sub output values for testing.

In accordance to still another aspect of the present disclosure, there is provided a learning device for training a deep learning based diagnostic model capable of diagnosing multi-cancer using biomarker group-related value information, including: at least one memory that stores instructions; and at least one processor configured to execute the instructions to perform: (I) in response to acquiring training data including the biomarker group-related value information and GT (Ground Truth) cancer information for each of patients, a process of inputting the training data into the diagnostic model and then instructing the diagnostic model to (i) allow each hidden layer, among a first hidden layer to a K-th hidden layer, to perform a fully connected operation on its previous sub input values for training obtained from its previous hidden layer, wherein K is an integer greater than or equal to 1, and then (ii) allow an output layer to perform a fully connected operation on K-th sub input values for training obtained from the K-th hidden layer, to thereby output multi-cancer diagnosis information for training as a result of predicting multi-cancer, wherein the learning device instructs the diagnostic model, while changing a value of k from 1 to K−1, (i) to input k-th sub output values for training outputted from a k-th hidden layer into a k-th probability layer and then to allow the k-th probability layer to output each of k-th probability values for training corresponding to each of L number of multi-cancers, (ii) (ii-1) to input the k-th sub output values for training into a k-th shortcut layer and then to allow the k-th shortcut layer to perform a fully connected operation on the k-th sub output values for training and then apply the k-th probability values for training as weights to a result of performing the fully connected operation on k-th sub output values for training, to thereby output k-th shortcut sub output values for training, and (ii-2) to input the k-th sub output values for training into a (k+1)-th hidden layer and then to allow the (k+1)-th hidden layer to perform a fully connected operation on the k-th sub output values for training and then apply "1−the k-th probability values for training" as weights to a result of performing the fully connected operation on the k-th sub output values for training, to thereby output a (k+1)-th sub output values for training, and (iii) to allow the output layer to perform the fully connected operation on (iii-1) the K-th sub output values for training outputted from the K-th hidden layer and (iii-2) a first shortcut sub output values for training outputted from a first shortcut layer to a (K−1)-th shortcut sub output values for training outputted from a (K−1)-th shortcut layer, to thereby output the multi-cancer diagnosis information for training; and (II) generating losses by referring to the multi-cancer diagnosis information for training outputted from the output layer and the GT cancer information, and backpropagating the losses to update parameters of at least one of the output layer, the K-th hidden layer to the first hidden layer, a (K−1)-th shortcut layer to a first shortcut layer, and a (K−1)-th probability layer to a first probability layer.

As one example, at the process of (I), the processor instructs the diagnostic model to input the k-th sub output values for training into the k-th probability layer and then to allow each of a (k_1)-th probability node of the k-th probability layer to a (k_L)-th probability node of the k-th probability layer, respectively corresponding to each of a first output node of the output layer related to a first cancer to an L-th output node of the output layer related to an L-th cancer, to perform a fully connected operation on the k-th sub output values for training, to thereby output a (k_1)-st probability value for training corresponding to the first cancer to a (k_L)-th probability value for training corresponding to the L-th cancer, as a result of predicting possibilities of progressing from the k-th hidden layer to the k-th shortcut layer without progressing from the k-th hidden layer to the (k+1)-th hidden layer.

As one example, at the process of (I), the processor instructs the diagnostic model to input the k-th sub output values for training into the k-th shortcut layer, which includes each of a (k_1)-st shortcut node to a (k_L)-th shortcut node corresponding to each of the first output node to the L-th output node, and then allow a (k_i)-th shortcut node corresponding to an i-th cancer among the (k_1)-st shortcut node to the (k_L)-th shortcut node to perform a fully connected operation on the k-th sub output values for training and then apply a (k_i)-th probability value for training as a weight to a result of performing the fully connected operation on the k-th sub output values for training, to thereby output a (k_i)-th shortcut sub output values for training.

As one example, at the process of (I), the processor instructs the diagnostic model to allow an i-th output node of the output layer corresponding to the i-th cancer to perform a fully connected operation on (i) the K-th sub output values for training of the K-th hidden layer, and (ii) a (1_i)-th shortcut sub output value for training outputted from a (1_i)-th shortcut node of the first shortcut layer to a ((K−1)_i)-th shortcut sub output value for training outputted from a ((K−1)_i)-th shortcut node of the (K−1)-th shortcut layer, to thereby output i-th cancer diagnosis information for training as a result of predicting the i-th cancer.

As one example, at the process of (I), the processor instructs the diagnostic model to input the k-th sub output values for training to the (k+1)-th hidden layer, and then to allow each of (k+1)-th hidden nodes of the (k+1)-th hidden layer to perform a fully connected operation on the k-th sub output values for training, and thus to sum each of (i) (k+1)_1-st intermediate sub output values for training, which are acquired by applying "1−the (k_1)-th probability value for training" as a weight to the results of performing the fully connected operation on the k-th sub output values for training, to (ii) (k+1)_L-th intermediate sub output values for training, which are acquired by applying "1−the (k_L)-th probability value for training" as a weight to the results of performing the fully connected operation on the k-th sub output values for training, to thereby output (k+1)-th sub output values for training.

In accordance with still yet another aspect of the present disclosure, there is provided a testing device for testing a deep learning based diagnostic model capable of diagnosing multi-cancer using biomarker group-related value information, including: at least one memory that stores instructions; and at least one processor configured to execute the instructions to perform: (I) a process of acquiring test data including specific biomarker group-related value information for a specific patient, on condition that the diagnostic model has been trained by a learning device through performing processes of, in response to acquiring training data including the biomarker group-related value information for training and GT (Ground Truth) cancer information for each of patients for training, inputting the training data into the diagnostic model and then instructing the diagnostic model to (i) allow each hidden layer, among a first hidden layer to a K-th hidden layer, to perform a fully connected operation on its previous sub input values for training obtained from its previous hidden layer, wherein K is an integer greater than or equal to 1, and then (ii) allow an output layer to perform a fully connected operation on K-th sub input values for training obtained from the K-th hidden layer, to thereby output multi-cancer diagnosis information for training as a result of predicting multi-cancer, wherein the learning device instructs the diagnostic model, while changing a value of k from 1 to K−1, (i) to input k-th sub output values for training outputted from a k-th hidden layer into a k-th probability layer and then to allow the k-th probability layer to output each of k-th probability values for training corresponding to each of L number of multi-cancers, (ii) (ii-1) to input the k-th sub output values for training into a k-th shortcut layer and then to allow the k-th shortcut layer to perform a fully connected operation on the k-th sub output values for training and then apply the k-th probability values for training as weights to a result of performing the fully connected operation on k-th sub output values for training, to thereby output k-th shortcut sub output values for training, and (ii-2) to input the k-th sub output values for training into a (k+1)-th hidden layer and then to allow the (k+1)-th hidden layer to perform a fully connected operation on the k-th sub output values for training and then apply "1−the k-th probability values for training" as weights to a result of performing the fully connected operation on the k-th sub output values for training, to thereby output a (k+1)-th sub output values for training, and (iii) to allow the output layer to perform the fully connected operation on (iii-1) the K-th sub output values for training outputted from the K-th hidden layer and (iii-2) a first shortcut sub output values for training outputted from a first shortcut layer to a (K−1)-th shortcut sub output values for training outputted from a (K−1)-th shortcut layer, to thereby output the multi-cancer diagnosis information for training; and (ii) generating losses by referring to the multi-cancer diagnosis information for training outputted from the output layer and the GT cancer information, and backpropagating the losses to update parameters of at least one of the output layer, the K-th hidden layer to the first hidden layer, a (K−1)-th shortcut layer to a first shortcut layer, and a (K−1)-th probability layer to a first probability layer; and (II) a process of inputting the test data into the diagnostic model and then instructing the diagnostic model to (i) allow each hidden layer, among the first hidden layer to the K-th hidden layer, to perform a fully connected operation on its previous sub input values for testing obtained from its previous hidden layer, wherein K is an integer greater than or equal to 1, and then (ii) allow the output layer to perform a fully connected operation on K-th sub input values for testing obtained from the K-th hidden layer, to thereby output multi-cancer diagnosis information for testing as a result of predicting multi-cancer, wherein the testing device instructs the diagnostic model, while changing a value of k from 1 to K−1, (i) to input k-th sub output values for testing outputted from the k-th hidden layer into the k-th probability layer and then to allow the k-th probability layer to output each of k-th probability values for testing corresponding to each of L number of multi-cancers, (ii) (ii-1) to input the k-th sub output values for testing into the k-th shortcut layer and then to allow the k-th shortcut layer to perform a fully connected operation on the k-th sub output values for testing and then apply the k-th probability values for testing as weights to a result of performing the fully connected operation on k-th sub output values for testing, to thereby output k-th shortcut sub output values for testing, and (ii-2) to input the k-th sub output values for testing into the (k+1)-th hidden layer and then to allow the (k+1)-th hidden layer to perform a fully connected operation on the k-th sub output values for testing and then apply "1−the k-th probability values for testing" as weights to a result of performing the fully connected operation on the k-th sub output values for testing, to thereby output a (k+1)-th sub output values for testing, and (iii) to allow the output layer to perform the fully connected operation on (iii-1) the K-th sub output values for testing outputted from the K-th hidden layer and (iii-2) a first shortcut sub output values for testing outputted from the first shortcut layer to the (K−1)-th shortcut sub output values for testing outputted from a (K−1)-th shortcut layer, to thereby output the multi-cancer diagnosis information for testing.

As one example, at the process of (II), the processor instructs the diagnostic model to input the k-th sub output values for testing into the k-th probability layer and then to allow each of a (k_1)-th probability node of the k-th probability layer to a (k_L)-th probability node of the k-th probability layer to perform a fully connected operation on the k-th sub output values for testing, to thereby output a (k_1)-st probability value for testing corresponding to the first cancer to a (k_L)-th probability value for testing corresponding to the L-th cancer, as a result of predicting possibilities of progressing from the k-th hidden layer to the k-th shortcut layer without progressing from the k-th hidden layer to the (k+1)-th hidden layer.

As one example, at the process of (II), the processor instructs the diagnostic model to input the k-th sub output values for testing into the k-th shortcut layer, and then allow a (k_i)-th shortcut node corresponding to an i-th cancer among the (k_1)-st shortcut node to the (k_L)-th shortcut node to perform a fully connected operation on the k-th sub output values for testing and then apply a (k_i)-th probability value for testing as a weight to a result of performing the fully connected operation on the k-th sub output values for testing, to thereby output a (k_i)-th shortcut sub output values for testing.

As one example, at the process of (II), the processor instructs the diagnostic model to allow the i-th output node of the output layer corresponding to the i-th cancer to perform a fully connected operation on (i) the K-th sub output values for testing of the K-th hidden layer, and (ii) a (1_i)-th shortcut sub output value for testing outputted from a (1_i)-th shortcut node of the first shortcut layer to a ((K−1)_i)-th shortcut sub output value for testing outputted from a ((K−1)_i)-th shortcut node of the (K−1)-th shortcut layer, to thereby output i-th cancer diagnosis information for testing as a result of predicting the i-th cancer.

As one example, at the process of (II), the processor instructs the diagnostic model to input the k-th sub output values for testing to the (k+1)-th hidden layer, and then to allow each of (k+1)-th hidden nodes of the (k+1)-th hidden layer to perform a fully connected operation on the k-th sub output values for testing, and thus to sum each of (i) (k+1)_1-st intermediate sub output values for testing, which are acquired by applying "1−the (k_1)-th probability value for testing" as a weight to the results of performing the fully connected operation on the k-th sub output values for testing, to (ii) (k+1)_L-th intermediate sub output values for testing, which are acquired by applying "1−the (k_L)-th probability value for testing" as a weight to the results of performing the fully connected operation on the k-th sub output values for testing, to thereby output (k+1)-th sub output values for testing.

In addition, recordable media that are readable by a computer for storing a computer program to execute the method of the present disclosure is further provided.

BRIEF DESCRIPTION OF THE DRAWINGS

The above and other objects and features of the present disclosure will become apparent from the following description of preferred embodiments given in conjunction with the accompanying drawings. The following drawings to be used to explain example embodiments of the present disclosure are only part of example embodiments of the present disclosure and other drawings can be obtained based on the drawings by those skilled in the art of the present disclosure without inventive work.

DETAILED DESCRIPTION OF THE PREFERRED EMBODIMENTS

Figure 1:
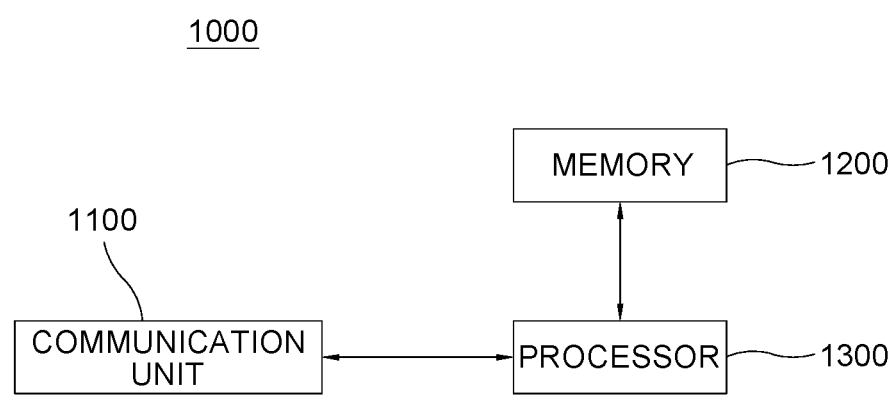
FIG. 1 is a diagram schematically illustrating a learning device for training a deep learning based diagnostic model capable of diagnosing multi-cancer using biomarker group-related value information in accordance with one example embodiment of the present disclosure.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the present invention, although different, are not necessarily mutually exclusive. For example, a particular feature, structure, or characteristic described herein in connection with one embodiment may be implemented within other embodiments without departing from the spirit and scope of the present invention. In addition, it is to be understood that the position or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

To allow those skilled in the art to carry out the present invention easily, the example embodiments of the present invention by referring to attached diagrams will be explained in detail as shown below.

FIG. 1 is a diagram schematically illustrating a learning device for training a deep learning based diagnostic model capable of diagnosing multi-cancer using biomarker group-related value information in accordance with one example embodiment of the present disclosure.

By referring to FIG. 1, the learning device 1000 may include a communication unit 1100 capable of acquiring training data which includes the biomarker group-related value information and GT cancer information for each of patients, a memory 1200 capable of storing instructions for the deep learning based diagnostic model to diagnose multi-cancer using the training data obtained from the communication unit 1100, and a processor 1300 capable of performing processes needed for training the deep learning based diagnostic model to diagnose multi-cancer by using the training data obtained from the communication unit 1100 and by using the instructions stored in the memory 1200.

Herein, the communication unit 1100 may acquire the training data from another device with the training data stored, or may acquire the training data from user inputs.

Specifically, the learning device 1000 may typically achieve a desired system performance by using combinations of at least one computing device and at least one computer software, e.g., a computer processor, a memory, a storage, an input device, an output device, or any other conventional computing components, an electronic communication device such as a router or a switch, an electronic information storage system such as a network-attached storage (NAS) and a storage area network (SAN) as the computing device and any instructions that allow the computing device to function in a specific manner as the computer software.

Also, the processors of such devices may include hardware configuration of MPU (Micro Processing Unit) or CPU (Central Processing Unit), cache memory, data bus, etc. Additionally, the computing device may further include operating system (OS) and software configuration of applications that achieve specific purposes.

Such description of the computing device does not exclude an integrated device including any combination of a processor, a memory, a medium, or any other computing components for implementing the present disclosure.

Following, the method for training the diagnostic model capable of diagnosing multi-cancer using the biomarker group-related value information in accordance with one example embodiment of the present disclosure as described above will be described with reference to FIG. 2.

First, the learning device 1000 may acquire the training data.

For example, the learning device 1000 may acquire the training data from another device with the training data stored, or may acquire the training data from user inputs through the communication unit 1100.

Herein, the training data may include the biomarker group-related value information and its corresponding GT cancer information for each of patients. Further, the GT cancer information for each of the patients may be cancer information procured from real-life patients and the number of cancer information may be more than one.

Furthermore, each of multiple pieces of the biomarker group-related value information may be each of values related to each of biomarkers for diagnosing multi-cancer. Herein, the biomarkers are indicators used for diagnosing cancer by using proteins, nucleic acids, metabolites, and the like included in a biological sample derived from a body of a patient, such as blood, urine, etc. Additionally, the training data may include information on age, gender, medical history, etc. for each of patients.

Next, the learning device 1000 inputs the training data into a diagnostic model 100 and then instructs the diagnostic model 100 to (i) allow each hidden layer, among a first hidden layer h_1 to a K-th hidden layer h_K, to perform a fully connected operation on its previous sub input values for training obtained from its previous hidden layer, and then (ii) allow an output layer 120 to perform a fully connected operation on K-th sub input values for training obtained from the K-th hidden layer h_K, to thereby output multi-cancer diagnosis information for training as a result of predicting multi-cancer. Herein the learning device 1000 instructs the diagnostic model 100, while changing a value of k from 1 to K−1, (i) to input k-th sub output values for training outputted from a k-th hidden layer into a k-th probability layer and then to allow the k-th probability layer to output each of k-th probability values for training corresponding to each of L number of multi-cancers, (ii) (ii-1) to input the k-th sub output values for training into a k-th shortcut layer and then to allow the k-th shortcut layer to perform a fully connected operation on the k-th sub output values for training and then apply the k-th probability values for training as weights to a result of performing the fully connected operation on k-th sub output values for training, to thereby output k-th shortcut sub output values for training, and (ii-2) to input the k-th sub output values for training into a (k+1)-th hidden layer and then to allow the (k+1)-th hidden layer to perform a fully connected operation on the k-th sub output values for training and then apply "1−the k-th probability values for training" as weights to a result of performing the fully connected operation on the k-th sub output values for training, to thereby output a (k+1)-th sub output values for training, and (iii) to allow the output layer 120 to perform the fully connected operation on (iii-1) the k-th sub output values for training outputted from the K-th hidden layer h_K and (iii-2) a first shortcut sub output values for training outputted from a first shortcut layer s_1 to a (K−1)-th shortcut sub output values for training outputted from a (K−1)-th shortcut layer s (K−1), to thereby output the multi-cancer diagnosis information for training. Herein, K may be an integer greater than or equal to 1.

That is, the learning device 1000 may input the training data into each diagnostic model 100.

Subsequently, the diagnostic model 100 may input each of input variables, for example, the biomarker group-related value information related to diagnosing multi-cancer, into each of nodes of an input layer 110.

And, the diagnostic model 100 may allow the first hidden layer h_1 to perform a fully connected operation on the input variables for training outputted from the input layer 110, to thereby output a first sub output values for training. Herein, the first sub output values for training of the first hidden layer h_1 may be expressed as follows.

$$h_1 = \phi(W_1 x + b_1)$$

From above, $\phi$ may be an activation function, and it may be any one of a sigmoid function, a hyperbolic tangent function, and a rectified linear unit function (ReLU), but it is not limited thereto.

Herein, $W_1$ may be a weight parameter of the first hidden layer h_1 and may be expressed as $W_1 \in R^{d_1 \times d}$, and $d_1$ and d may be the number of nodes of the first hidden layer h_1 and the number of nodes for the input layer 110, respectively.

Furthermore, $b_1$ may be a bias parameter for each node of the first hidden layer h_1 and may be expressed as $b_1 \in R^{d_1}$.

Afterward, the diagnostic model 100 may input the first sub output values for training into the first probability layer p_1, and instruct the first probability layer p_1 to output each of first probability values for training corresponding to each of L number of cancers.

Herein, the first probability layer h_1 may include a (1_1)-st probability node to a (1_L)-th probability node, respectively corresponding to each of a first output node of the output layer 120 related to a first cancer to an L-th output node of the output layer 120 related to an L-th cancer for classifying the L number of cancers. Moreover, each of the (1_1)-st probability node to the (1_L)-th probability node may perform a fully connected operation on the first sub output values for training, to thereby output a (1_1)-st probability value for training corresponding to the first cancer to a (1_L)-th probability value for training corresponding to the L-th cancer, as a result of predicting possibilities of progressing from the first hidden layer h_1 to the first shortcut layer s_1 without progressing from the first hidden layer h_1 to the second hidden layer h_2. Herein, the (1_1)-st probability value for training outputted from the (1_1)-st probability node to the (1_L)-th probability value for training outputted from the (1_L)-th probability node may be expressed as follow.

$$P_{1i} = \sigma(h_1^T \beta_{1i} + \beta_{1i0})$$

Herein, $\sigma$, which may be a sigmoid function, stands for an activation function, $\beta_{1i}$ stands for a weight parameter, and $\beta_{1i0}$ stands for a bias parameter of a first probability layer p_1. Herein i=1, . . . , L.

Next, the diagnostic model 100 may (i) input the first sub output values for training into the first shortcut layer s_1, (ii) allow the first shortcut layer s_1 to perform a fully connected operation on the first sub output values for training and (iii) apply the first probability values for training as weights to a result of performing the fully connected operation on the first sub output values for training, to thereby output first shortcut sub output values for training.

Herein, the first shortcut layer s_1 may include a (1_1)-st shortcut node to a (1_L)-th shortcut node respectively corresponding to the first output node to the L-th output node of the output layer 120. Additionally, each of the (1_1)-st shortcut node to the (1_L)-th shortcut node may perform a fully connected operation on the first sub output values for training and then apply each of the first probability values for training as weights to a result of performing the fully connected operation on the first sub output values for training, to thereby output the first shortcut sub output values for training. That is, (i) the (1_1)-st shortcut node may perform a fully connected operation on the first sub output values for training and apply a (1_1)-st probability value for training as a weight to a result of performing the fully connected operation on the first sub output values for training, to thereby output a (1_1)-st shortcut sub output value for training, and (ii) the (1_L)-th shortcut node may perform a fully connected operation on the first sub output values for training and apply a (1_L)-th probability value for training as a weight to a result of performing the fully connected operation on the first sub output values for training, to thereby output a (1_L)-th shortcut sub output value for training. Herein, the (1_1)-st shortcut sub output value for training outputted from the (1_1)-st shortcut node to the (1_L)-th shortcut sub output value for training outputted from the (1_L)-th shortcut node may be expressed as follow.

$$S_{1i} = P_{1i}(h_1^T + \gamma_{1i0})$$

Herein, $\gamma_{1i}$ stands for a weight parameter of the first shortcut layer s_1, $\gamma_{1i0}$ stands for a bias parameter of the first shortcut layer s_1. Herein i=1, . . . , L.

Next, the diagnostic model 100 may input the first sub output values for training into a second hidden layer h_2, allow the second hidden layer h_2 to perform a fully connected operation on the first sub output values for training and then apply "1−first probability values for training" as weights to a result of performing the fully connected operation on the first sub output values for training, to thereby output second shortcut sub output values for training.

That is, each of second nodes of the second hidden layer h_2 may perform a fully connected operation on the first sub output values for training, and thus to sum each of (i) 2_1-st intermediate sub output values for training, which are acquired by applying "1−the (1_1)-th probability value for training" as a weight to the results of performing the fully connected operation on the first sub output values for training, to (ii) 2_L-th intermediate sub output values for training, which are acquired by applying "1−the (1_L)-th probability value for training" as a weight to the results of performing the fully connected operation on the first sub output values for training, to thereby output a second sub output values for training. Herein, the second sub output values outputted from the second hidden layer h_2 may be expressed as follow.

$$h_2 = \sum_{i=1}^{L}(1 - P_{1i})\phi(W_2 h_1 + b_2)$$

Herein, $W_2$ stands for a weight parameter of the second hidden layer h_2, and may be expressed as $W_2 \in R^{d_2 \times d_1}$, in which $d_2$ stands for the number of nodes of the second hidden layer h_2.

Further, $b_2$ may be a bias parameter for each node of the second hidden layer h_2 and may be expressed as $b_2 \in R^{d_2}$.

With such method, operations of a second probability layer p_2 and the second shortcut layer s_2 to the (K−1)-th probability layer p_(K−1) and the (K−1)-th shortcut layer s_(K−1) may all be performed by using each of the second sub output values for training of the second hidden layer h_2 to (K−1)-th sub output values for training of a (K−1)-th hidden layer h_(K−1).

That is, the diagnostic model 100 inputs the k-th sub output values for training into the k-th probability layer and then allow each of a (k_1)-th probability node of the k-th probability layer to a (k_L)-th probability node of the k-th probability layer to perform a fully connected operation on the k-th sub output values for training, to thereby output a (k_1)-st probability value for training corresponding to the first cancer to a (k_L)-th probability value for training corresponding to the L-th cancer, as a result of predicting possibilities of progressing from the k-th hidden layer to the k-th shortcut layer without progressing from the k-th hidden layer to the (k+1)-th hidden layer. Herein, the (k_1)-st probability value for training to the (k_L)-th probability value for training may be expressed as follow.

$$P_{ki} = \sigma(h_k^T \beta_{ki} + \beta_{ki0})$$

Herein, $\beta_{ki}$ stands for a weight parameter of the k-th probability layer and may be expressed as $\beta_{ki} \in R^{d_k}$, in which $\beta_{ki0}$ stands for a bias parameter of the k-th probability layer and may be expressed as $\beta_{ki0} \in R$. Herein, k=1, ..., K−1.

Furthermore, the diagnostic model 100 inputs the k-th sub output values for training into the k-th shortcut layer, and allow a (k_i)-th shortcut node corresponding to an i-th cancer among the (k_1)-st shortcut node to the (k_L)-th shortcut node to perform a fully connected operation on the k-th sub output values for training and then to apply a (k_i)-th probability value for training as a weight to a result of performing the fully connected operation on the k-th sub output values for training, to thereby output a (k_i)-th shortcut sub output values for training. Herein, the (k_i)-th shortcut sub output values for training may be expressed as follow.

$$S_{ki} = P_{ki}(h_k^T \gamma_{ki} + \gamma_{ki0})$$

Herein, $\gamma_{ki}$ stands for a weight parameter of the k-th shortcut layer and may be expressed as $\gamma_{ki} \in R^{d_k}$, and $\gamma_{ki0}$ stands for a bias paremeter of the k-th shortcut layer and may be expressed as $\gamma_{ki0} \in R$.

Additionally, the diagnostic model 100 inputs the k-th sub output values for training into the (k+1)-th hidden layer, and allows each of (k+1)-th hidden nodes of the (k+1)-th hidden layer to perform a fully connected operation on the k-th sub output values for training and thus sums each of (i) (k+1)_1-st intermediate sub output values for training, which are acquired by applying "1−the (k_1)-th probability value for training" as a weight to the results of performing the fully connected operation on the k-th sub output values for training, to (ii) (k+1)_L-th intermediate sub output values for training, which are acquired by applying "1−the (k_L)-th probability value for training" as a weight to the results of performing the fully connected operation on the k-th sub output values for training, to thereby output (k+1)-th sub output values for training. Herein the (k+1) sub output values may be expressed as follow.

$$h_{k+1} = \sum_{i=1}^{L}(1 - P_{ki})\phi(W_{k+1}h_k + b_{k+1})$$

Herein, $W_{k+1}$ stands for a weight parameter of the (k+1)-th hidden layer and may be expressed as $W_{k+1} \in R^{d_{k+1} \times d_k}$, and $b_{k+1}$ stands for a bias parameter for each node of the (k+1)-th hidden layer, and may be expressed as $b_{k+1} \in R^{d_{k+1}}$.

Next, the diagnostic model 100 allows an i-th output node of the output layer 120 corresponding to the i-th cancer to perform a fully connected operation on (i) the K-th sub output values for training of the K-th hidden layer h_K, and (ii) a (1_i)-th shortcut sub output value for training outputted from a (1_i)-th shortcut node of the first shortcut layer s_1 to a ((K−1)_i)-th shortcut sub output value for training outputted from a ((K−1)_i)-th shortcut node of the (K−1)-th shortcut layer s_(K−1), to thereby output i-th cancer diagnosis information for training as a result of predicting the i-th cancer.

Herein, outputs of the output layer 120 of y=(y_1, ..., y_L) may be expressed as follow.

$$y_i = (h_{K+1})_i + \sum_{k=1}^{K-1} S_{ki}$$

Herein, $h_{K+1} = W_{K+1}h_K + b_{K+1}$, and $(h_{K+1})_i$ stands for a result related to the i-th cancer of $h_{K+1}$. Also, $W_{K+1} \in R^{L \times d_K}$ and $b_{K+1} \in R^L$.

Next, the learning device 1000 may generate losses by referring to the multi-cancer diagnosis information for training outputted from the output layer 120 and the GT cancer information. As one example, the learning device 1000 may input the multi-cancer diagnosis information for training and the GT cancer information into a loss layer 200, to thereby allow the loss layer 200 to generate losses.

Further, the learning device 1000 may train the diagnostic model 100 through backpropagating the losses to update parameters of at least one of the output layer 120, the K-th hidden layer h_K to the first hidden layer h_1, the (K−1)-th shortcut layer s_(K−1) to the first shortcut layer s_1, and the (K−1)-th probability layer p_(K−1) to the first probability layer p_1.

The deep learning based diagnostic model trained through this method may efficiently diagnose a cancer of a patient from the biomarker group-related value information because some pieces of the biomarker group-related value information related to easily classifiable cancers will be calculated through the shortcut layer, and other some pieces of the biomarker group-related value information related to difficultly classifiable cancers will be calculated through the hidden layers.

As described above, on condition that the deep learning based diagnostic model 100 capable of diagnosing multi-cancer using the biomarker group-related value information has been trained, a testing method and a testing device for testing the deep learning based diagnostic model 100 capable of diagnosing multi-cancer using the biomarker group-related value information will be described in detail as below.

Figure 3:
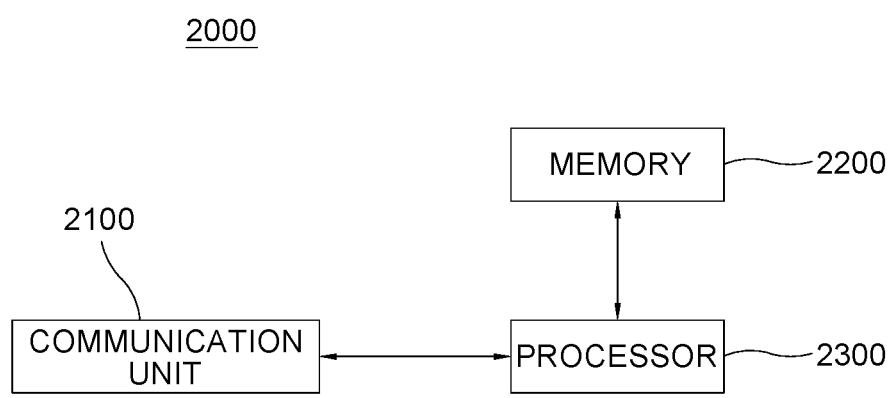
FIG. 3 is a diagram schematically illustrating a testing device for testing the deep learning based diagnostic model capable of diagnosing the multi-cancer using the biomarker group-related value information in accordance with one example embodiment of the present disclosure.

FIG. 3 is a diagram schematically illustrating a testing device for testing the diagnostic model 100 capable of diagnosing the multi-cancer using the biomarker group-related value information in accordance with one example embodiment of the present disclosure.

By referring to FIG. 3, the testing device 2000 may include a communication unit 2100 capable of acquiring test data which includes a piece of specific biomarker group-related value information for a specific patient, a memory 2200 capable of storing instructions for testing the deep learning based diagnostic model 100 by using the test data which includes the specific biomarker group-related value information obtained from the communication unit 2100, and a processor 2300 capable of performing processes needed for testing the diagnostic model 100 by using the test data obtained from the communication unit 2100 and by using the instructions stored in the memory 2200.

Herein, the communication unit 2100 may acquire the test data of the specific biomarker group-related value information of the specific patient from another device that generates the test data, or may acquire the test data of the specific biomarker group-related value information of the specific patient from user inputs.

Specifically, the testing device 2000 may typically achieve a desired system performance by using combinations of at least one computing device and at least one computer software, e.g., a computer processor, a memory, a storage, an input device, an output device, or any other conventional computing components, an electronic communication device such as a router or a switch, an electronic information storage system such as a network-attached storage (NAS) and a storage area network (SAN) as the computing device and any instructions that allow the computing device to function in a specific manner as the computer software.

Also, the processors of such devices may include hardware configuration of MPU (Micro Processing Unit) or CPU (Central Processing Unit), cache memory, data bus, etc. Additionally, the computing device may further include operating system (OS) and software configuration of applications that achieve specific purposes.

Such description of the computing device does not exclude an integrated device including any combination of a processor, a memory, a medium, or any other computing components for implementing the present disclosure.

Figure 4:
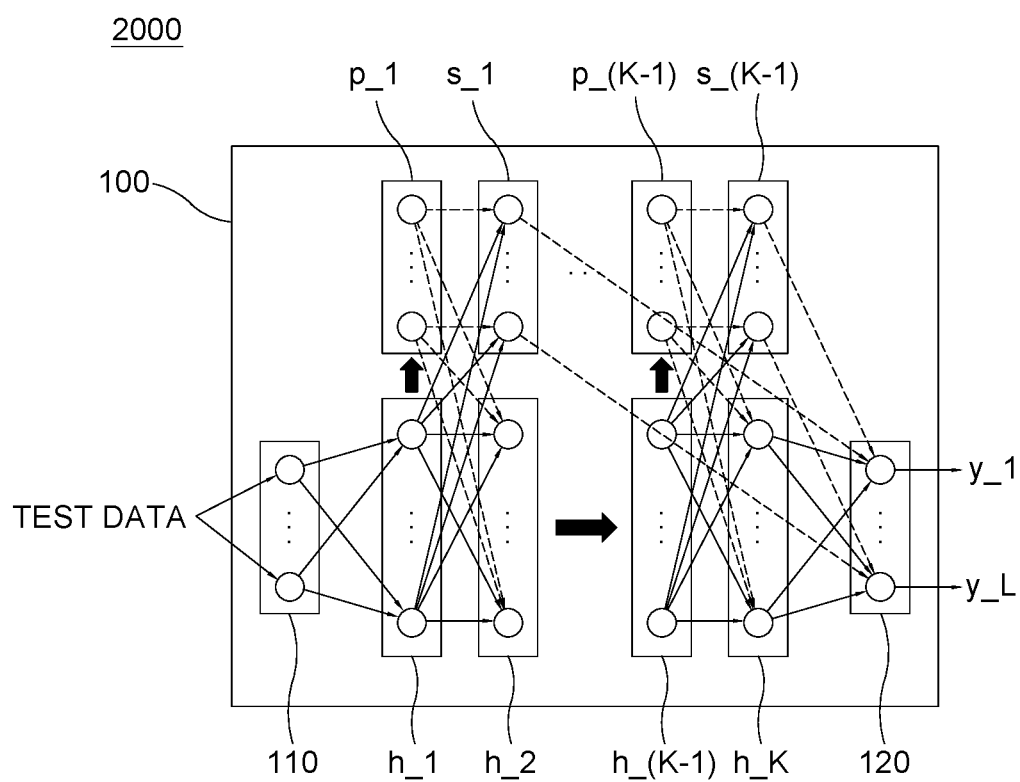
FIG. 4 is a diagram schematically illustrating a method for testing the deep learning based diagnostic model capable of diagnosing the multi-cancer using the biomarker group-

Following, the method for testing the diagnostic model 100 capable of diagnosing multi-cancer using the biomarker group-related value information in accordance with one example embodiment of the present disclosure as described above will be described with reference to FIG. 4. Hereinafter, for parts easily deducible from the explanation of FIG. 2 will be omitted.

Figure 2:
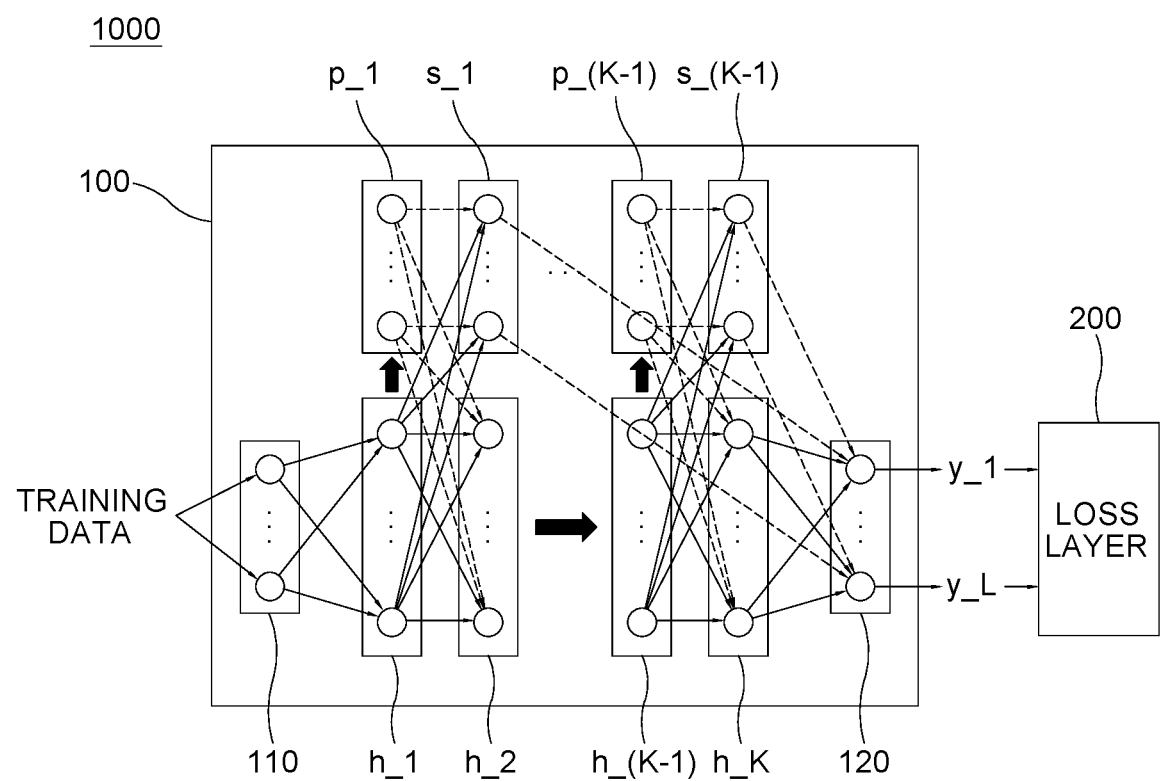
FIG. 2 is a diagram schematically illustrating a method for training the deep learning based diagnostic model capable of diagnosing the multi-cancer using the biomarker group-related value information in accordance with one example embodiment of the present disclosure.

First, on condition that the deep learning based diagnostic model 100 capable of diagnosing multi-cancer using the biomarker group-related value information is trained as explained in detail with reference to FIG. 2, the testing device 2000 may acquire the test data of the specific biomarker group-related value information of the specific patient for diagnosing multi-cancer.

As an example, the testing device 2000 may acquire the test data through interacting with another device that may generate the test data including the specific biomarker group-related value information of the specific patient from the communication unit 2100, or may acquire the test data of the specific biomarker group-related value information of the specific patient from the user inputs.

Next, the testing device 2000 inputs the test data into a diagnostic model 100 and then instructs the diagnostic model 100 to (i) allow each hidden layer, among the first hidden layer h_1 to the K-th hidden layer h_K, to perform a fully connected operation on its previous sub input values for testing obtained from its previous hidden layer, and then (ii) allow the output layer 120 to perform a fully connected operation on K-th sub input values for testing obtained from the K-th hidden layer h_K, to thereby output multi-cancer diagnosis information for testing as a result of predicting multi-cancer. Herein the testing device 2000 instructs the diagnostic model 100, while changing a value of k from 1 to K−1, (i) to input k-th sub output values for testing outputted from the k-th hidden layer into the k-th probability layer and then to allow the k-th probability layer to output each of k-th probability values for testing corresponding to each of L number of multi-cancers, (ii) (ii-1) to input the k-th sub output values for testing into the k-th shortcut layer and then to allow the k-th shortcut layer to perform a fully connected operation on the k-th sub output values for testing and then apply the k-th probability values for testing as weights to a result of performing the fully connected operation on k-th sub output values for testing, to thereby output k-th shortcut sub output values for testing, and (ii-2) to input the k-th sub output values for testing into the (k+1)-th hidden layer and then to allow the (k+1)-th hidden layer to perform a fully connected operation on the k-th sub output values for testing and then apply "1–the k-th probability values for testing" as weights to a result of performing the fully connected operation on the k-th sub output values for testing, to thereby output a (k+1)-th sub output values for testing, and (iii) to allow the output layer 120 to perform the fully connected operation on (iii-1) the K-th sub output values for testing outputted from the K-th hidden layer h_K and (iii-2) a first shortcut sub output values for testing outputted from the first shortcut layer s_1 to a (K−1)-th shortcut sub output values for testing outputted from the (K−1)-th shortcut layer s_(K−1), to thereby output the multi-cancer diagnosis information for testing.

That is, the testing device 2000 may input the test data into diagnostic model 100.

For example, the diagnostic model 100 may input each of input variables, for example, the biomarker group-related value information related to diagnosing multi-cancer, into each of nodes of the input layer 110.

And, the diagnostic model 100 may allow the first hidden layer h_1 to perform a fully connected operation on the input variables for testing outputted from the input layer 110, to thereby output a first sub output values for testing.

Afterward, the diagnostic model 100 may input the first sub output values for testing into the first probability layer p_1, to thereby output each of first probability values for testing corresponding to each of L number of cancers.

Herein, each of the (1_1)-st probability node to the (1_L)-th probability node of the first probability layer p_1 may perform a fully connected operation on the first sub output values for testing, to thereby output a (1_1)-st probability value for testing corresponding to the first cancer to a (1_L)-th probability value for testing corresponding to the L-th cancer, as a result of predicting possibilities of progressing from the first hidden layer h_1 to the first shortcut layer s_1 without progressing from the first hidden layer h_1 to the second hidden layer h_2.

Next, the diagnostic model 100 may (i) input the first sub output values for testing into the first shortcut layer s_1, (ii) allow the first shortcut layer s_1 to perform a fully connected operation on the first sub output values for testing, and (iii) then apply the first probability values for testing as weights to a result of performing the fully connected operation on the first sub output values for testing, to thereby output first shortcut sub output values for testing.

Herein, each of the (1_1)-st shortcut node to the (1_L)-th shortcut node of the first shortcut layer s_1 may perform a fully connected operation on the first sub output values for testing and then apply each of the first probability values as weights to a result of performing the fully connected operation on the first sub output values for testing, to thereby output the first shortcut sub output values for testing. That is, (i) the (1_1)-st shortcut node may perform a fully connected operation on the first sub output values for testing and apply a (1_1)-st probability value for testing as a weight to a result of performing the fully connected operation on the first sub output values for testing, to thereby output a (1_1)-st shortcut sub output value for testing, and (ii) the (1_L)-th shortcut node may perform a fully connected operation on the first sub output values for testing and apply a (1_L)-th probability value for testing as a weight to a result of performing the fully connected operation on the first sub output values for testing, to thereby output a (1_L)-th shortcut sub output value for testing.

Additionally, the diagnostic model 100 may input the first sub output values for testing into a second hidden layer h_2, allow the second hidden layer h_2 to perform a fully connected operation on the first sub output values for testing and then apply "1−first probability values for testing" as weights to a result of performing the fully connected operation on the first sub output values for testing, to thereby output second shortcut sub output values for testing.

That is, each of second nodes of the second hidden layer h_2 may perform a fully connected operation on the first sub output values for testing, and thus to sum each of (i) 2_1-st intermediate sub output values for testing, which are acquired by applying "1−the (1_1)-th probability value for testing" as a weight to the results of performing the fully connected operation on the first sub output values for testing, to (ii) 2_L-th intermediate sub output values for testing, which are acquired by applying "1−the (1_L)-th probability value for testing" as a weight to the results of performing the fully connected operation on the first sub output values for testing, to thereby output a second sub output values for testing.

With such method, operations of a second probability layer p_2 and the second shortcut layer s_2 to the (K−1)-th probability layer p_(K−1) and the (K−1)-th shortcut layer s_(K−1) may all be performed by using each of the second sub output values for testing of the second hidden layer h_2 to (K−1)-th sub output values for testing of a (K−1)-th hidden layer h_(K−1).

That is, the diagnostic model 100 inputs the k-th sub output values for testing into the k-th probability layer and then allow each of a (k_1)-th probability node of the k-th probability layer to a (k_L)-th probability node of the k-th probability layer to perform a fully connected operation on the k-th sub output values for testing, to thereby output a (k_1)-st probability value for testing corresponding to the first cancer to a (k_L)-th probability value for testing corresponding to the L-th cancer, as a result of predicting possibilities of progressing from the k-th hidden layer to the k-th shortcut layer without progressing from the k-th hidden layer to the (k+1)-th hidden layer.

Further, the diagnostic model 100 inputs the k-th sub output values for testing into the k-th shortcut layer, and allow a (k_i)-th shortcut node corresponding to an i-th cancer among the (k_1)-st shortcut node to the (k_L)-th shortcut node to perform a fully connected operation on the k-th sub output values for testing and then to apply a (k_i)-th probability value for testing as a weight to a result of performing the fully connected operation on the k-th sub output values for testing, to thereby output a (k_i)-th shortcut sub output values for testing.

Furthermore, the diagnostic model 100 inputs the k-th sub output values for testing to the (k+1)-th hidden layer, and allows each of (k+1)-th hidden nodes of the (k+1)-th hidden layer to perform a fully connected operation on the k-th sub output values for testing, and thus sums each of (i) (k+1)_1-st intermediate sub output values for testing, which are acquired by applying "1−the (k_1)-th probability value for testing" as a weight to the results of performing the fully connected operation on the k-th sub output values for testing, to (ii) (k+1)_L-th intermediate sub output values for testing, which are acquired by applying by "1−the (k_L)-th probability value for testing" as a weight to the results of performing the fully connected operation on the k-th sub output values for testing, to thereby output (k+1)-th sub output values for testing.

Next, the diagnostic model 100 allows an i-th output node of the output layer 120 corresponding to the i-th cancer to perform a fully connected operation on (i) the K-th sub output values for testing of the K-th hidden layer h_K, and (ii) a (1_i)-th shortcut sub output value for testing outputted from a (1_i)-th shortcut node of the first shortcut layer to a ((K−1)_i)-th shortcut sub output value for testing outputted from a ((K−1)_i)-th shortcut node of the (K−1)-th shortcut layer s_(K−1), to thereby output i-th cancer diagnosis information for testing as a result of predicting the i-th cancer.

Herein, the diagnostic model 100 may output a specific cancer corresponding to the highest probability value among the probability values for each of a first cancer to the L-th cancer outputted from the output layer 120 as a cancer diagnosis for the specific patient.

According to such method, the deep learning based diagnostic model 100 may efficiently diagnose a cancer of the patient from the biomarker group-related value information because the biomarker group-related value information related to easily classifiable cancers will be calculated through the shortcut layer, and the biomarker group-related value information related to difficultly classifiable cancers will be calculated through hidden layers.

The present disclosure has an effect of providing a deep learning based diagnostic model that can classify data related to easily classifiable cancers through a simpler structure, and classify other data related to difficultly classifiable cancers through a complex structure.

The present disclosure has another effect of accurately identifying various types of cancers by using the biomarker group-related value information.

The present disclosure has still another effect of accurately identifying various types of cancers by implementing a statistical discrimination method using the biomarker group-related value information.

The present disclosure has still yet another effect of improving a reliability in classifying the various types of cancers by implementing the statistical discrimination method using the biomarker group-related value information.

The embodiments of the present disclosure as explained above can be implemented in a form of executable program command through a variety of computer means recordable to computer readable media. The computer readable media may include solely or in combination, program commands, data files, and data structures. The program commands recorded to the media may be components specially designed for the present disclosure or may be usable to a skilled human in a field of computer software. Computer readable media include magnetic media such as hard disk, floppy disk, and magnetic tape, optical media such as CD-ROM and DVD, magneto-optical media such as floptical disk and hardware devices such as ROM, RAM, and flash memory specially designed to store and carry out program commands. Program commands may include not only a machine language code made by a complier but also a high level code that can be used by an interpreter etc., which is executed by a computer. The aforementioned hardware device can work as more than a software module to perform the action of the present disclosure and they can do the same in the opposite case.

As seen above, the present disclosure has been explained by specific matters such as detailed components, limited embodiments, and drawings. They have been provided only to help more general understanding of the present disclosure. It, however, will be understood by those skilled in the art that various changes and modification may be made from the description without departing from the spirit and scope of the disclosure as defined in the following claims.

Accordingly, the thought of the present disclosure must not be confined to the explained embodiments, and the following patent claims as well as everything including variations equal or equivalent to the patent claims pertain to the category of the thought of the present disclosure.

What is claimed is:

1. A method for training a deep learning based diagnostic model capable of diagnosing multi-cancer using biomarker group-related value information, comprising steps of:
    (a) a learning device, in response to acquiring training data including the biomarker group-related value information and GT (Ground Truth) cancer information for each of patients, inputting the training data into the diagnostic model and then instructing the diagnostic model to (i) allow each hidden layer, among a first hidden layer to a K-th hidden layer, to perform a fully connected operation on its previous sub input values for training obtained from its previous hidden layer, wherein K is an integer greater than or equal to 1, and then (ii) allow an output layer to perform a fully connected operation on K-th sub input values for training obtained from the K-th hidden layer, to thereby output multi-cancer diagnosis information for training as a result of predicting multi-cancer, wherein the multi-cancer diagnosis information for training is output by the diagnostic model with the learning device instructing the diagnostic model, while changing a value of k from 1 to K−1, (i) to input k-th sub output values for training outputted from a k-th hidden layer into a k-th probability layer and then to allow the k-th probability layer to output each of k-th probability values for training corresponding to each of L number of multi-cancers, (ii) (ii-1) to input the k-th sub output values for training into a k-th shortcut layer and then to allow the k-th shortcut layer to perform a fully connected operation on the k-th sub output values for training and then apply the k-th probability values for training as weights to a result of performing the fully connected operation on k-th sub output values for training, to thereby output k-th shortcut sub output values for training, and (ii-2) to input the k-th sub output values for training into a (k+1)-th hidden layer and then to allow the (k+1)-th hidden layer to perform a fully connected operation on the k-th sub output values for training and then apply "1−the k-th probability values for training" as weights to a result of performing the fully connected operation on the k-th sub output values for training, to thereby output a (k+1)-th sub output values for training, and (iii) to allow the output layer to perform the fully connected operation on (iii-1) the K-th sub output values for training outputted from the K-th hidden layer and (iii-2) a first shortcut sub output values for training outputted from a first shortcut layer to a (K−1)-th shortcut sub output values for training outputted from a (K−1)-th shortcut layer; and
    (b) the learning device generating losses by referring to the multi-cancer diagnosis information for training outputted from the output layer and the GT cancer information, and backpropagating the losses to update parameters of at least one of the output layer, the K-th hidden layer to the first hidden layer, a (K−1)-th shortcut layer to a first shortcut layer, and a (K−1)-th probability layer to a first probability layer.

2. The method of claim 1, wherein, at the step of (a), the learning device instructs the diagnostic model to input the k-th sub output values for training into the k-th probability layer and then to allow each of a (k_1)-th probability node of the k-th probability layer to a (k_L)-th probability node of the k-th probability layer, respectively corresponding to each of a first output node of the output layer related to a first cancer to an L-th output node of the output layer related to an L-th cancer, to perform a fully connected operation on the k-th sub output values for training, to thereby output a (k_1)-st probability value for training corresponding to the first cancer to a (k_L)-th probability value for training corresponding to the L-th cancer, as a result of predicting possibilities of progressing from the k-th hidden layer to the k-th shortcut layer without progressing from the k-th hidden layer to the (k+1)-th hidden layer.

3. The method of claim 2, wherein, at the step of (a), the learning device instructs the diagnostic model to input the k-th sub output values for training into the k-th shortcut layer, which includes each of a (k_1)-st shortcut node to a (k_L)-th shortcut node corresponding to each of the first output node to the L-th output node, and then allow a (k_i)-th shortcut node corresponding to an i-th cancer among the (k_1)-st shortcut node to the (k_L)-th shortcut node to perform a fully connected operation on the k-th sub output values for training and then apply a (k_i)-th probability value for training as a weight to a result of performing the fully connected operation on the k-th sub output values for training, to thereby output a (k_i)-th shortcut sub output values for training.

4. The method of claim 3, at the step of (a), the learning device instructs the diagnostic model to allow an i-th output node of the output layer corresponding to the i-th cancer to perform a fully connected operation on (i) the K-th sub output values for training of the K-th hidden layer, and (ii) a (1_i)-th shortcut sub output value for training outputted from a (1_i)-th shortcut node of the first shortcut layer to a ((K−1)_i)-th shortcut sub output value for training outputted from a ((K−1)_i)-th shortcut node of the (K−1)-th shortcut layer, to thereby output i-th cancer diagnosis information for training as a result of predicting the i-th cancer.

5. The method of claim 2, wherein, at the step of (a), the learning device instructs the diagnostic model to input the k-th sub output values for training to the (k+1)-th hidden layer, and then to allow each of (k+1)-th hidden nodes of the (k+1)-th hidden layer to perform a fully connected operation on the k-th sub output values for training, and thus to sum each of (i) (k+1)_1-st intermediate sub output values for training, which are acquired by applying "1−the (k_1)-th probability value for training" as a weight to the results of performing the fully connected operation on the k-th sub output values for training, to (ii) (k+1)_L-th intermediate sub output values for training, which are acquired by applying "1−the (k_L)-th probability value for training" as a weight to the results of performing the fully connected operation on the k-th sub output values for training, to thereby output (k+1)-th sub output values for training.

6. A learning device for training a deep learning based diagnostic model capable of diagnosing multi-cancer using biomarker group-related value information, comprising:
at least one memory that stores instructions; and
at least one processor configured to execute the instructions to perform: (I) in response to acquiring training data including the biomarker group-related value information and GT (Ground Truth) cancer information for each of patients, a process of inputting the training data into the diagnostic model and then instructing the diagnostic model to (i) allow each hidden layer, among a first hidden layer to a K-th hidden layer, to perform a fully connected operation on its previous sub input values for training obtained from its previous hidden layer, wherein K is an integer greater than or equal to 1, and then (ii) allow an output layer to perform a fully connected operation on K-th sub input values for training obtained from the K-th hidden layer, to thereby output multi-cancer diagnosis information for training as a result of predicting multi-cancer, wherein the multi-cancer diagnosis information for training is output by the diagnostic model with the learning device instructing the diagnostic model, while changing a value of k from 1 to K−1, (i) to input k-th sub output values for training outputted from a k-th hidden layer into a k-th probability layer and then to allow the k-th probability layer to output each of k-th probability values for training corresponding to each of L number of multi-cancers, (ii) (ii-1) to input the k-th sub output values for training into a k-th shortcut layer and then to allow the k-th shortcut layer to perform a fully connected operation on the k-th sub output values for training and then apply the k-th probability values for training as weights to a result of performing the fully connected operation on k-th sub output values for training, to thereby output k-th shortcut sub output values for training, and (ii-2) to input the k-th sub output values for training into a (k+1)-th hidden layer and then to allow the (k+1)-th hidden layer to perform a fully connected operation on the k-th sub output values for training and then apply "1−the k-th probability values for training" as weights to a result of performing the fully connected operation on the k-th sub output values for training, to thereby output a (k+1)-th sub output values for training, and (iii) to allow the output layer to perform the fully connected operation on (iii-1) the K-th sub output values for training outputted from the K-th hidden layer and (iii-2) a first shortcut sub output values for training outputted from a first shortcut layer to a (K−1)-th shortcut sub output values for training outputted from a (K−1)-th shortcut layer; and (II) generating losses by referring to the multi-cancer diagnosis information for training outputted from the output layer and the GT cancer information, and backpropagating the losses to update parameters of at least one of the output layer, the K-th hidden layer to the first hidden layer, a (K−1)-th shortcut layer to a first shortcut layer, and a (K−1)-th probability layer to a first probability layer.

7. The learning device of claim 6, wherein, at the process of (I), the processor instructs the diagnostic model to input the k-th sub output values for training into the k-th probability layer and then to allow each of a (k_1)-th probability node of the k-th probability layer to a (k_L)-th probability node of the k-th probability layer, respectively corresponding to each of a first output node of the output layer related to a first cancer to an L-th output node of the output layer related to an L-th cancer, to perform a fully connected operation on the k-th sub output values for training, to thereby output a (k_1)-st probability value for training corresponding to the first cancer to a (k_L)-th probability value for training corresponding to the L-th cancer, as a result of predicting possibilities of progressing from the k-th hidden layer to the k-th shortcut layer without progressing from the k-th hidden layer to the (k+1)-th hidden layer.

8. The learning device of claim 7, wherein, at the process of (I), the processor instructs the diagnostic model to input the k-th sub output values for training into the k-th shortcut layer, which includes each of a (k_1)-st shortcut node to a (k_L)-th shortcut node corresponding to each of the first output node to the L-th output node, and then allow a (k_i)-th shortcut node corresponding to an i-th cancer among the (k_1)-st shortcut node to the (k_L)-th shortcut node to perform a fully connected operation on the k-th sub output values for training and then apply a (k_i)-th probability value for training as a weight to a result of performing the fully connected operation on the k-th sub output values for training, to thereby output a (k_i)-th shortcut sub output values for training.

9. The learning device of claim 8, wherein, at the process of (I), the processor instructs the diagnostic model to allow an i-th output node of the output layer corresponding to the i-th cancer to perform a fully connected operation on (i) the K-th sub output values for training of the K-th hidden layer, and (ii) a (1_i)-th shortcut sub output value for training outputted from a (1_i)-th shortcut node of the first shortcut layer to a ((K−1)_i)-th shortcut sub output value for training outputted from a ((K−1)_i)-th shortcut node of the (K−1)-th shortcut layer, to thereby output i-th cancer diagnosis information for training as a result of predicting the i-th cancer.

10. The learning device of claim 7, wherein, at the process of (I), the processor instructs the diagnostic model to input the k-th sub output values for training to the (k+1)-th hidden layer, and then to allow each of (k+1)-th hidden nodes of the (k+1)-th hidden layer to perform a fully connected operation on the k-th sub output values for training, and thus to sum each of (i) (k+1)_1-st intermediate sub output values for training, which are acquired by applying "1−the (k_1)-th probability value for training" as a weight to the results of performing the fully connected operation on the k-th sub output values for training, to (ii) (k+1)_L-th intermediate sub output values for training, which are acquired by applying "1−the (k_L)-th probability value for training" as a weight to the results of performing the fully connected operation on the k-th sub output values for training, to thereby output (k+1)-th sub output values for training.

* * * * *